United States Patent [19]

McAleer et al.

[11] 4,217,418

[45] Aug. 12, 1980

[54] RECOVERY OF SMALL PARTICLES BY FLOW CENTRIFUGATION

[75] Inventors: William J. McAleer, Ambler; William M. Hurni, North Wales, both of Pa.

[73] Assignee: Merck & Co., Inc., Rahway, N.J.

[21] Appl. No.: 18,385

[22] Filed: Mar. 9, 1979

Related U.S. Application Data

[63] Continuation-in-part of Ser. No. 904,097, May 8, 1978, abandoned.

[51] Int. Cl.² .................. A61K 39/12; C12K 7/00
[52] U.S. Cl. .................. 435/239; 260/112 B; 424/89; 210/78
[58] Field of Search .................. 210/65, 70–72, 210/77, 78, DIG. 23; 260/112 B; 424/89; 435/239

[56] References Cited

U.S. PATENT DOCUMENTS

| | | | |
|---|---|---|---|
| 3,838,144 | 9/1974 | Leach | 424/89 |
| 3,994,870 | 11/1976 | Neurath et al. | 260/112 B |
| 4,017,360 | 4/1977 | Bertland et al. | 424/89 |
| 4,024,243 | 5/1977 | McAleer et al. | 260/112 B |
| 4,088,748 | 5/1978 | McAleer et al. | 424/89 |
| 4,113,712 | 9/1978 | Funakoshi | 424/89 |

OTHER PUBLICATIONS

Nat. Cancer Institute Monogram 21: pp. 253–283 (1966).

Takahashi et al., "Large Scale Isolation of Dane Particles from Plasma Containing Hepatitis B Antigen and Demonstration of a Circular Double Stranded DNA Molecule Extruding Directly from their Cores"; Journal of Immunology, vol. 117, No. 4, Oct. 1976, pp. 1392–1397.

*Primary Examiner*—Benoit Castel
*Attorney, Agent, or Firm*—Donald J. Perrella; Julian S. Levitt

[57] ABSTRACT

It has now been found that small size particles may be extracted from a proteinaceous liquid at a low flow rate in flow-centrifuge operation by precooling the liquid before it enters the centrifuge and by employing a multistep gradient.

6 Claims, No Drawings

RECOVERY OF SMALL PARTICLES BY FLOW CENTRIFUGATION

RELATED APPLICATION

This application is a continuation-in-part of our copending application Ser. No. 904,097 filed May 8, 1978, now abandoned.

BACKGROUND OF THE INVENTION

In any centrifuge containing a density gradient, the gradient material tends to diffuse from an area of high concentration to an area of low concentration even against high centrifugal forces.

In a flow centrifuge the material flowing across the gradient front enters the rotor at the center and travels to the front of the gradient on one radial path, the inflow channel, and returns on another radial path, the outflow channel, leaving behind in the gradient the particles desired to be separated. The high centrifugal forces acting on the material as it is traveling radially are exactly balanced so that very little pressure is required to flow liquid through the rotor at speed.

Despite forward diffusion of the gradient material against the gravitational field, the gradient material does not enter the inflow radial channel because there is a constant inflow of liquid pushing the gradient material back into the rotor. In the case of the outflow radial channel, however, the gradient material can diffuse into this channel with the result that the density of the liquid in the outflow radial channel becomes greater than that of the inflow radial channel. The resulting imbalance in the density of the material in the inflow radial channel versus the outflow radial channel renders flow of material impossible (gradient lock).

OBJECTS OF THE INVENTION

It is an object of the present invention to extract small size particles from proteinaceous liquids in flow-centrifuge operations. Another object is to eliminate gradient lock in continuous flow centrifuge operations. A further object is to provide a method for the direct extraction of $HB_sAg$ from plasma. These and other objects of the present invention will be apparent from the following description.

SUMMARY OF THE INVENTION

It has now been found that small size particles may be extracted from a proteinaceous liquid at a low flow rate in flow-centrifuge operation by precooling the liquid before it enters the centrifuge and by employing a multi-step gradient.

DETAILED DESCRIPTION

In the case of extracting hepatitis B surface antigen ($HB_sAg$) from a biological fluid such as, for example, plasma, the problem of gradient lock is magnified for several reasons:

1. It is necessary to flow a large amount of plasma through the rotor at one time.
2. The $HB_sAg$ particle is extremely small, about 1/5 the size of an average virus particle, and it is necessary to employ a very low flow rate which rate is selected in order to obtain efficient extraction of the $HB_sAg$, i.e. an extraction efficiency of about 70% or above. At high flow rates the extraction efficiency declines drastically. In the K6 flow centrifuge, a low flow rate is from about 1.5 to about 2.5 liters per hour.
3. The use of a very low flow increases the residence time which is required for efficient extraction. It also results in an imbalance between the density of the inlet material and outlet material as at low flow rates the outflow material contains less low density inlet material and so the density gradient component of the outflow material is not diluted by low density inlet material as much as it would be at a high flow rate.
4. The forward diffusion takes place at a rate dependent only on the centrifugal force and the physical characteristics of the gradient material itself. Thus, at a low flow rate, less outflow material will be present to dilute the dense gradient material moving forward than at a high flow rate.
5. Plasma contains signficant amounts of proteinaceous matter which is liable to coagulate due to heat generated in the rotating seal of the centrifuge especially at low flow rates. Therefore, the plasma must be cooled just prior to entering the centrifuge.
6. Coarse filtration of the plasma must be done shortly prior to feeding the plasma into the centrifuge because debris will reform after filtration has been carried out and clog the narrow channels in the flow centrifuge.

It has been found, however, according to the present invention that small size particles, i.e., particles having a size up to about 50 nm may be extracted from a proteinaceous liquid at a low flow rate in flow-centrifuge operation by precooling the liquid before it enters the centrifuge and by employing a multi-step gradient.

By a proteinaceous liquid is meant a liquid containing proteins such as, for example, plasma. By a low flow rate is meant one which provides efficient extraction of the small size particles from the proteinaceous liquid, i.e., an extraction efficiency of about 70% or above. At high flow rates the extraction efficiency declines drastically. In the K6 flow centrifuge, a low flow rate is from about 1.5 to about 2.5 liters/hour. By a multi-step gradient is meant one containing a sufficient number of steps so that the density differential between any two adjacent steps is sufficiently small to reduce forward diffusion of the gradient sufficiently to prevent gradient lock. By a coarse filter is meant one which removes flocculent material which develops in plasma on standing.

Before feeding into the flow centrifuge, the plasma is cooled to a temperature which prevents coagulation within the centrifuge where considerable amounts of heat are generated, particularly at the rotating seal of the centrifuge. This temperature is usually about 0° C.

The following example illustrates the present invention without, however, limiting the same thereto.

EXAMPLE 1

20 Liters of plasma from hepatitis B donors are pooled in preparation for the extraction procedure.

The K6 low centrifuge rotor is assembled and completely filled with 3,500 ml of phosphate buffered saline (PBS). Then 1,600 ml of PBS buffer is partially displaced by pumping in sequentially 400 ml of 10% sucrose, 400 ml of 25% sucrose, 400 ml of 40% sucrose and 400 ml of 60% sucrose.

The centrifuge rotor is accelerated to 35,000 rpm for the run. As the run begins the plasma, which contains various proteinaceous debris and floccular components which require removal, is passed through a 293 mm millipore filter holder with the filter support pad acting as a coarse filter. The material is then passed through a cooling coil kept at 0° C. to precool the plasma just prior to entering into the centrifuge. This is necessary in order to avoid coagulation of the plasma protein by heat generated at the rotating seal at the low flow rate being used.

The back pressure to flow through the centrifuge is then monitored with time and the flow rate monitored with time to maintain flow rate of 2 liters per hour. The low flow rate is necessary in order to extract the protein particles of interest, ($HB_sAg$) from the plasma. It is necessary to keep the back pressure below 15 pounds/sq. in. in order to keep the plasma from leaking out around the rotating seal of the centrifuge. The following is a table of flow rates and back pressure for a typical run:

| Time (minutes) | Back Pressure | Flow Rate |
|---|---|---|
| 0 | 2 | |
| 5 | 0 | 2160 ml/hr |
| 25 | 0 | |
| 40 | 0.5 | |
| 55 | 2.0 | 2400 ml/hr |
| 70 | 2.0 | |
| 85 | 3.0 | |
| 115 | 5.5 | |
| 145 | 5.5 | |
| 325 | 5.5 | 2040 ml/hr |
| 385 | 5.5 | 2040 ml/hr |
| 445 | 7.5 | 2220 ml/hr |
| 455 | end of run | |

At the end of the flow period (~8 hours) the centrifuge is deaccelerated to 15,000 rpm so that buffer can be flowed through the rotor at acceptable back pressure to clean the plasma protein away from the rotating seals. If this is not done, residual proteins will coagulate and clog the rotor making it impossible to remove the gradient from the rotor intact. After the buffer is flowed through (~200 ml), the rotor is reaccelerated to 35,000 rpm for 1 hour of residence time. The rotor is then brought to rest and the gradient removed. A typical gradient at the end of the run is as follows:

| Cut No. | Volume | % Sucrose |
|---|---|---|
| 1 | 450 ml | 42 |
| 2 | 450 ml | 40 |
| 3 | 450 ml | 35 |
| 4 | 450 ml | 29 |
| 5 | 450 ml | 24 |
| 6 | 450 ml | 19 |
| 7 | 450 ml | 14 |
| 8 | 250 ml | 9 |

The foregoing conditions allow one to successfully flow large quantities of plasma through a flow rotor and extract $HB_sAg$ therefrom.

What is claimed is:

1. In a continuous flow centrifugation process for the direct extraction of small size particles from a proteinaceous liquid wherein the proteinaceous liquid is continuously fed to the flow centrifuge and extracted proteinaceous liquid is continuously withdrawn from the flow centrifuge during extraction under conditions which favor formation of gradient lock, the improvement comprising removing flocculent material from the proteinaceous liquid, pre-cooling the proteinaceous liquid before feeding it to the flow centrifuge, feeding the proteinaceous liquid at a low flow rate effective to provide efficient extraction of the small size particles as the proteinaceous liquid passes through the flow centrifuge which contains a multi-step gradient wherein the density differential between adjacent gradient densities is sufficiently small to prevent gradient lock.

2. A process according to claim 1 wherein the proteinaceous liquid is plasma.

3. A process according to claim 1 wherein the flow rate is one which permits coagulation of a protein in the proteinaceous liquid in the absence of pre-cooling.

4. A process according to claim 1 wherein the multi-step gradient comprises sucrose.

5. A process according to claim 1 wherein the multi-step gradient comprises about 10% sucrose, about 25% sucrose, about 40% sucrose and about 60% sucrose.

6. A process according to claim 1 wherein the small size particle is $HB_sAg$.

* * * * *